United States Patent [19]

Schneider et al.

[11] Patent Number: 5,290,567
[45] Date of Patent: Mar. 1, 1994

[54] PULVERULENT PRODUCTS COMPOSED OF A WATER-INSOLUBLE CORE SUBSTANCE AND OF A PROTECTIVE COVERING

[75] Inventors: Joachim U. Schneider, Weisenheim; Gerhard Schwarz, Harthausen; Paul Grafen, Weisenheim; Wolfgang Bewert, Frankenthal; Horst Schumacher, Bobenheim, all of Fed. Rep. of Germany

[73] Assignee: BASF Aktiengesellschaft, Ludwigshafen, Fed. Rep. of Germany

[21] Appl. No.: 894,126

[22] Filed: Jun. 4, 1992

[30] Foreign Application Priority Data

Jun. 25, 1991 [DE] Fed. Rep. of Germany ....... 4120918

[51] Int. Cl.$^5$ ................................................ A61K 9/14
[52] U.S. Cl. .................................. 424/489; 424/490; 424/486; 424/484
[58] Field of Search ................ 424/489, 486, 484, 490

[56] References Cited

U.S. PATENT DOCUMENTS

| | | | |
|---|---|---|---|
| 3,499,962 | 3/1970 | Wurzburg et al. | 424/489 |
| 4,519,961 | 5/1985 | Schumacher et al. | 264/4.6 |
| 4,935,245 | 6/1990 | Horn | 424/489 |
| 4,940,588 | 7/1990 | Sparks | 424/489 |

FOREIGN PATENT DOCUMENTS

| | | |
|---|---|---|
| 0074050 | 8/1982 | European Pat. Off. . |
| 0343993 | 11/1989 | European Pat. Off. . |
| WO91/07949 | 6/1991 | PCT Int'l Appl. . |
| 1072795 | 6/1967 | United Kingdom . |

Primary Examiner—Thurman K. Page
Assistant Examiner—William E. Benston, Jr.
Attorney, Agent, or Firm—Keil & Weinkauf

[57] ABSTRACT

Pulverulent products composed of a water-insoluble core substance and of a protective covering, are obtainable by
- dispersing the core substance in an aqueous solution of amylose or a starch with an amylose content of more than 40% by weight as film-forming polymer for the protective covering,
- spraying this dispersion using hydrophobic silica as auxiliary and
- subsequently drying the sprayed particles.

6 Claims, No Drawings

PULVERULENT PRODUCTS COMPOSED OF A WATER-INSOLUBLE CORE SUBSTANCE AND OF A PROTECTIVE COVERING

The present invention relates to pulverulent products composed of a water-insoluble core substance and of a protective covering, obtainable by
- dispersing the core substance in an aqueous solution of amylose or a starch with an amylose content of more than 40% by weight as film-forming polymer for the protective covering,
- spraying this dispersion using hydrophobic silica as auxiliary and
- subsequently drying the sprayed particles.

The present invention also relates to a process for preparing the pulverulent products composed of a water-insoluble core substance and of a protective covering.

Pulverulent products composed of a water-insoluble core substance such as, in particular, vitamins and carotenoids and of a protective covering are generally known and are used in pharmaceutical processing and in the human and animal food sectors.

U.S. Pat. No. 3 499 962 discloses pulverulent products composed of water-insoluble core substances such as perfumes or vitamins and of a protective covering composed of starch with an amylose content above 40% by weight, and GB-A 10 72 795 describes the use of amylose as film-forming polymer for encapsulating vitamins. However, the disadvantage is the conversion of the dispersion into the pulverulent products, which either is too industrially elaborate or provides particles which are too small.

EP-A 00 74 050 discloses the preparation of dry powders by spraying a dispersion with the addition of hydrophobic silica as auxiliary and subsequent drying.

It is an object of the present invention to provide pulverulent products of the said type which are more easily obtainable industrially and have better technical properties than the preparations hitherto disclosed.

We have found that this object is achieved by the pulverulent products, defined in the first paragraph, composed of a water-insoluble core substance and of a protective covering, and by a process for preparing these pulverulent products.

Film-forming polymers to be used according to the invention are starch with an amylose content above 40% by weight or, preferably, amylose, which are generally employed in amounts of from 30 to 99% of the weight of the pulverulent product.

The amylose can be obtained from corn starch which contains from 20 to 30% by weight of amylose in addition to from 80 to 70% by weight of amylopectin. Starch with an amylose content of at least 40% by weight can be obtained from novel varieties of corn with high amylose contents or from marrowfat peas.

The amylose or starch with a high amylose content to be used according to the invention has the advantage that it is soluble in water only at elevated temperature and separates out as water-insoluble film on cooling. Protective coverings of this type are therefore distinguished by high thermal and mechanical stability and resistance to water. The products prepared in this way can thus be processed even in very stressful ways such as extrusion or compression.

A solution of the film-forming polymers can be produced either batchwise at from 150° to 160° C. in an autoclave or, preferably, continuously with steam under from 5 to 10 bar by means of a heated nozzle (jet heater).

Suitable and preferred water-insoluble core substances are pharmaceutical agents, flavorings and, in particular, vitamins and carotenoids. Further suitable examples are fats, oils and perfumes.

The amount of the water-insoluble core substance to be encapsulated is usually from 1 to 40% of the weight of the pulverulent product.

To prepare the dispersion, the core substance is dispersed in an aqueous solution of the film-forming polymer, it being possible for the dispersion to contain additives such as antioxidants, emulsifiers and/or preservatives, plasticizers, stabilizers, complexing agents or further film-formers.

The subsequent spraying of the dispersion is carried out with the aid of an auxiliary, and hydrophobic silica is used according to the invention (Die Mühle und Mischfuttertechnik, 114, (1977) 3). Hydrophobic silica comprises silica particles whose free hydroxyl groups on the surface have been reacted with a hydrophobic compound such as, in particular, a haloalkylsilane, for example dimethyldichlorosilane.

The introduction of the spraying auxiliary and its atomization are carried out with air at about 2-5 $m^3$/kg of auxiliary, the amount of auxiliary required being only from 0.02 to 0.15 times that of the dispersion.

It is preferable to use a spraying tower and to introduce the hydrophobic silica, with simultaneous dispersion, into the spraying chamber at from 25° to 30° C.

It is expedient to introduce the spraying auxiliary above the atomizing device, for example it is possible to use nozzles or high-speed atomizing disks.

The temperature of the dispersion to be atomized is not critical. It is normally from 60° to 90° C.

The direct introduction of the hydrophobic silica into the spraying zone substantially avoids mechanical stress on the particles. The thin hydrophobic film of the spraying auxiliary formed during the spraying stabilizes the particles so that agglomeration of the particles on contact in the non-solidified state is prevented and immediate drying is possible in a subsequent fluidized bed drier in a conventional manner.

The drying is generally carried out at from 30° to 80° C. because with air at this temperature the excess hydrophobic silica escapes.

The pulverulent products which can be obtained in a straightforward manner by the process according to the invention are distinguished by high stability, such as insolubility in hot water, and are composed of particles with a satisfactory surface. The spraying procedure is such that, in a conventional manner, the particles have an average particle size of from 100 to 600 $\mu$m, in particular from 180 to 350 $\mu$m. Powders with this particle size range ensure adequate protection of the encapsulated core substance and are particularly suitable for processing, for example to human or animal foods.

EXAMPLES

Preparation of pulverulent products

A suspension of a % by weight of a film-forming polymer P in b % of water was heated at $T_1$° C. for t minutes and, after a further 20 minutes, cooled to 80° C. over the course of 90 minutes. The mixture was then mixed with a solution of c % by weight of additive A in d % by weight of water and maintained at 80° C. for 10 minutes.

Subsequently e % by weight of core substance K were added and stirred into the solution over the course of 10 minutes.

Subsequently the dispersion was sprayed under f bar and at 80° C. in air loaded with hydrophobic silica. 10 kg of silica were added per h, and 80 kg of aqueous dispersion were sprayed per h. Conventional drying in a fluidized bed at 30° C. (Examples 1 to 4) or 60° C. (Example 5) provided the powder with a residual water content of g % and an active substance content of h IU/g or i %.

The particles were assessed by determining the particle size distribution by ASTM screen analysis.

Particles with sizes from 100 to 600 μm, with a peak at about 180–350 μm, were obtained in every case.

Details of the experiments are to be found in Tables 1 and 2.

Meanings of the abbreviations in the tables
Polymer P
P/1 corn starch with an amylose content of 70%
P/2 marrowfat pea starch with an amylose content of 75%
Additive A
A/1 preswelled gelatin (film-former)
A/2 glucose syrup (plasticizer)
Core substance K
K/1 vitamin A acetate ($2.23 \times 10^6$ IU/g), stabilized with ethoxyquin
K/2 vitamin A acetate ($2.12 \times 10^6$ IU/g), stabilized with ethoxyquin
K/3 vitamin E acetate (24.7%)
K/4 citranaxanthin (33.2%)
K/5 vitamin A acetate ($2.15 \times 10^6$ IU/g), stabilized with ethoxyquin

TABLE 1

| Preparation of pulverulent products | | | | | |
|---|---|---|---|---|---|
| | Examples | | | | |
| | 1 | 2 | 3 | 4 | 5* |
| Polymer P | P/1 | P/2 | P/1 | P/1 | P/1 |
| a [% by wt.] | 153.3 | 102 | 221.6 | 233 | 15.3 |
| b [% by wt.] | 550 | 550 | 900 | 1000 | 58 |
| t [min] | 55 | 55 | 20 | 20 | |
| $T_i$ [°C.] | 150 | 150 | 150 | 150 | 163 |
| Additive A | A/1 & A/2 | A/2 | | | |
| c [% by wt.] | 17.2 & 67.4 | 56.3 | | | |
| d [% by wt.] | 200 | 200 | | | |
| Core substance K | K/1 | K/2 | K/3 | K/4 | K/5 |
| e [% by wt.] | 77.7 | 51.8 | 85 | 54.6 | 5.1 |
| f [bar] | 4.8 | 4.8 | 5 | 5 | 12 |
| g [%] | 2 | 3.2 | 2.7 | 2.3 | 4.7 |
| h [IU/g] | 603000 | 506000 | | | 532200 |
| i [%] | | | 24.7 | 7.2 | |

*continuous starch digestion in a jet heater under 6 bar

TABLE 2

| Particle size distribution of the pulverulent products | | | | | |
|---|---|---|---|---|---|
| | Examples | | | | |
| | 1 | 2 | 3 | 4 | 5 |
| Particle size [μm] | 1 | 2 | 3 | 4 | 5 |
| >500 | 2.6 | 2.6 | 10.1 | 6.4 | 4.2 |
| >425 | 3.8 | 2.3 | 11.5 | 6.2 | 11.2 |
| >355 | 10.1 | 4.1 | 14.1 | 9.0 | 21.8 |
| >250 | 55.2 | 19.0 | 28.4 | 30.3 | 38.0 |
| >180 | 16.5 | 37.7 | 25.6 | 31.6 | 18.8 |
| >125 | 7.5 | 24.7 | 9.3 | 15.5 | 5.4 |
| >106 | 2.1 | 7.5 | 1.0 | 0.7 | 0.6 |

We claim:

1. A pulverulent product having an average particle size of from 100 to 600 μm and which particles are insoluble in hot water, said particles being composed of a water-insoluble core substance and a protective covering, obtained by dispersing the core substance in an aqueous solution of amylose or a starch with an amylose content of more than 40% by weight as film-forming polymer for the protective covering, spraying this dispersion using hydrophobic silica as auxiliary and subsequently drying the sprayed particles.

2. A pulverulent product composed of a water-insoluble core substance and of a protective covering as defined in claim 1, containing vitamins or carotenoids as the water-insoluble core substance.

3. A pulverulent product composed of a water-insoluble core substance and of a protective covering as defined in claim 1, wherein from 2 to 15% by weight of hydrophobic silica, based on the aqueous dispersion, is used as the auxiliary.

4. A pulverulent product composed of a water-insoluble core substance and of a protective covering as defined in claim 2, wherein from 2 to 15% by weight of hydrophobic silica, based on the aqueous dispersion, is used as the auxiliary.

5. A pulverulent product as defined in claim 1, wherein the average particle diameter is from 180 to 350 μm.

6. A process for preparing a pulverulent product composed of a water-insoluble core substance and a protective covering which comprises:

dispersing the water-insoluble core substance having an average particle size of from 100 to 600 mm and which particles are insoluble in hot water in an aqueous solution of a film-forming amylose or starch polymer having an amylose content of more than 40% by weight, spraying the dispersion with the aid of hydrophobic silica as a spraying auxiliary, and subsequently drying the sprayed product.

* * * * *